US005099831A

United States Patent [19]

Freed

[11] Patent Number: 5,099,831

[45] Date of Patent: Mar. 31, 1992

[54] POSTURE IMPROVEMENT DEVICE

[76] Inventor: William L. Freed, 21 Fairway La., Trumbull, Conn. 06611

[21] Appl. No.: 619,884

[22] Filed: Nov. 29, 1990

[51] Int. Cl.[5] .................... A61F 5/00

[52] U.S. Cl. .................... 128/24.2; 128/24 R; 128/33; 482/131; 482/130

[58] Field of Search .................... 128/69-75, 128/83; 272/126, 136, 144

[56] References Cited

U.S. PATENT DOCUMENTS

| | | | |
|---|---|---|---|
| Re. 32,791 | 11/1988 | Saunders | 128/75 |
| 3,621,839 | 11/1971 | Barthe | 128/75 |
| 3,771,158 | 11/1973 | Greissing | 128/71 |
| 3,828,377 | 8/1974 | Fary, Sr. | 5/327 B |
| 4,166,459 | 9/1979 | Nightingale | 128/75 |
| 4,191,949 | 3/1980 | Myers | 340/573 |
| 4,320,749 | 3/1982 | Highley | 128/83 |
| 4,503,844 | 3/1985 | Siczek | 128/71 |
| 4,520,800 | 6/1985 | Kowalski | 128/72 |
| 4,736,736 | 4/1988 | Moers et al. | 128/75 |
| 4,951,654 | 8/1990 | Gabale et al. | 128/75 |

OTHER PUBLICATIONS

Kendall et al., *Posture and Pain*, 1967, pp. 123, 153-154, 156-161.

Kendall et al., *Muscles Testing and Function*, 1983, pp. 106, 112,114-116, 301.

Cailliet, *Shoulder Pain*, 1981, p. 44.

Harper & Row, Publishers, *Management of Common Musculoskeletal Disorders*, 1983, p. 286.

*Primary Examiner*—Richard J. Apley

*Assistant Examiner*—Linda C. M. Dvorak

*Attorney, Agent, or Firm*—Fish & Richardson

[57] ABSTRACT

A device for improving posture by providing thoracic extension, having a base portion with a head support and arm supports disposed at the head-end section of the base. A flexible membrane is provided which extends upward from the surface of the base on which the patient reclines. As posterior forces are applied to the arm rests, a system of pulleys and cables effects an upward displacement of the flexible membrane into the back of the patient. The flexible membrane is projected into the thoracic spine of the patient and effectively stretches certain of the back muscles in order to strengthen them for posture purposes. Furthermore, the device allows the patient to isolate either a middle or lower trapezius muscles of the back so as to apply the thoracic extension by the flexible membrane.

8 Claims, 3 Drawing Sheets

POSTURE IMPROVEMENT DEVICE

FIELD OF THE INVENTION

The present invention is directed to devices which improve the posture of a patient.

BACKGROUND OF THE INVENTION

Various painful and pathological conditions can be attributed to poor posture as it relates to the thoracic spine. The poor posture of the thoracic spine may be in the form of increased thoracic kyphosis, an abnormal rearward curvature of the spine, with accompanying forward depressed shoulders.

One of the conditions associated with poor posture is referred to as the thoracic outlet syndrome. In this condition, neurovascular structures are irritated during passage between the pectoralis minor muscle and the coracoid process. The condition is caused by an adaptive shortening of the pectoralis minor muscle as it relates to the postural fault of the particular patient.

Another condition associated with poor posture is chronic mid-back pain. This painful syndrome is directly related to a slow gradual strain to the middle and upper back musculature. A prolonged postural fault will eventually lead to an adaptive stretching of the middle and lower trapezius muscles, as well as a shortening of the pectoralis minor muscle.

Various conventional devices have been utilized in order to address faulty thoracic posture. The most common corrective device is the use of a brace. However, the usage of such a support system to hold the shoulders of a patient back has not proven to be effective over long periods of time. With the accompanying straps and harness, a shoulder brace may reduce some of the symptoms associated with mid-back strain, but such devices typically do not serve to correct the poor posture. In fact, the use of such support systems may further weaken the middle and lower trapezius muscles as they reduce the workload normally associated with these muscles. Furthermore, due to the degree of discomfort required in order to support a patient's forward depressed shoulders with such a strapping system, usage by the patient over a prolonged period of time may not be possible. In addition, due to the strap placement associated with such a support system, it is not uncommon to actually cause further irritation of the neurovascular structure as it passes under the pectoralis minor muscle.

Other attempts have been proposed to improve posture, such as warning devices which sound when a patient begins to conform to a slumping posture. However, such devices are merely palliative rather than therapeutic for correcting such postural faults. Also, many believe that the use of rowing machines, to strengthen the muscles of the middle back, will improve posture. However, the strengthening of the rhomboid muscles with the use of rowing machines actually rotates the glenoid cavity downward and elevates the scapula, which in turn actually worsens the postural fault of forward shoulders and upper back strain.

SUMMARY OF THE INVENTION

Accordingly, it is an object of this invention to provide an exercise device which includes both active and passive components to improve a posture of a patient.

It is a further object of the invention to provide a device which isolates the middle and lower trapezius muscles of a patient's back while simultaneously providing thoracic extension to stretch the pectoralis minor muscle of the patient.

BRIEF DESCRIPTION OF THE DRAWINGS

We turn now to a detailed description of the preferred embodiment, after first briefly describing the drawings.

DETAILED DESCRIPTION OF THE ILLUSTRATED EMBODIMENTS

Figure 1:
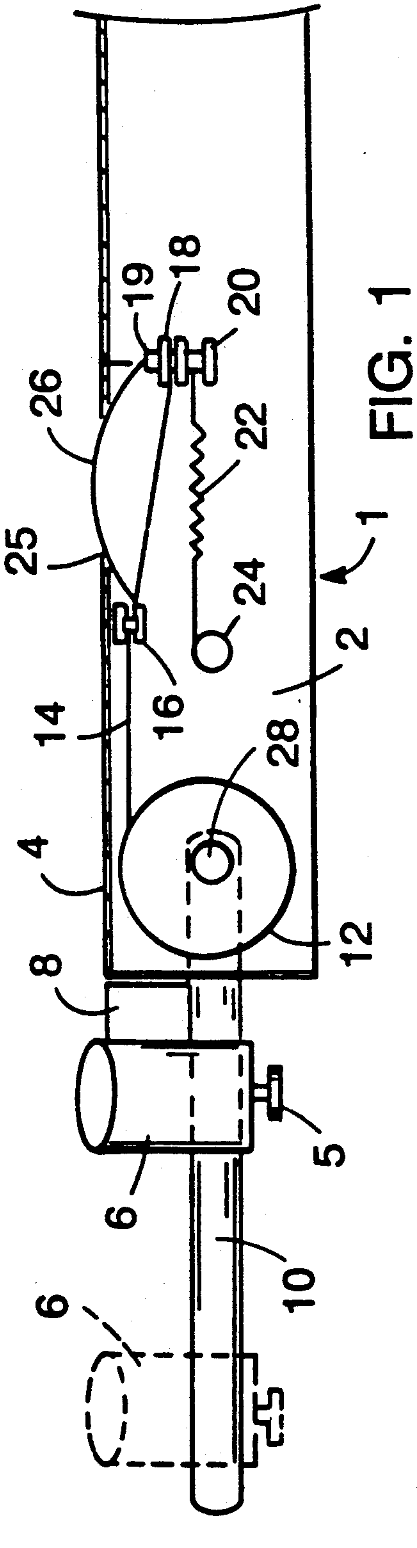
FIG. 1 is a side view of the posture improvement apparatus of this invention.
Figure 2:
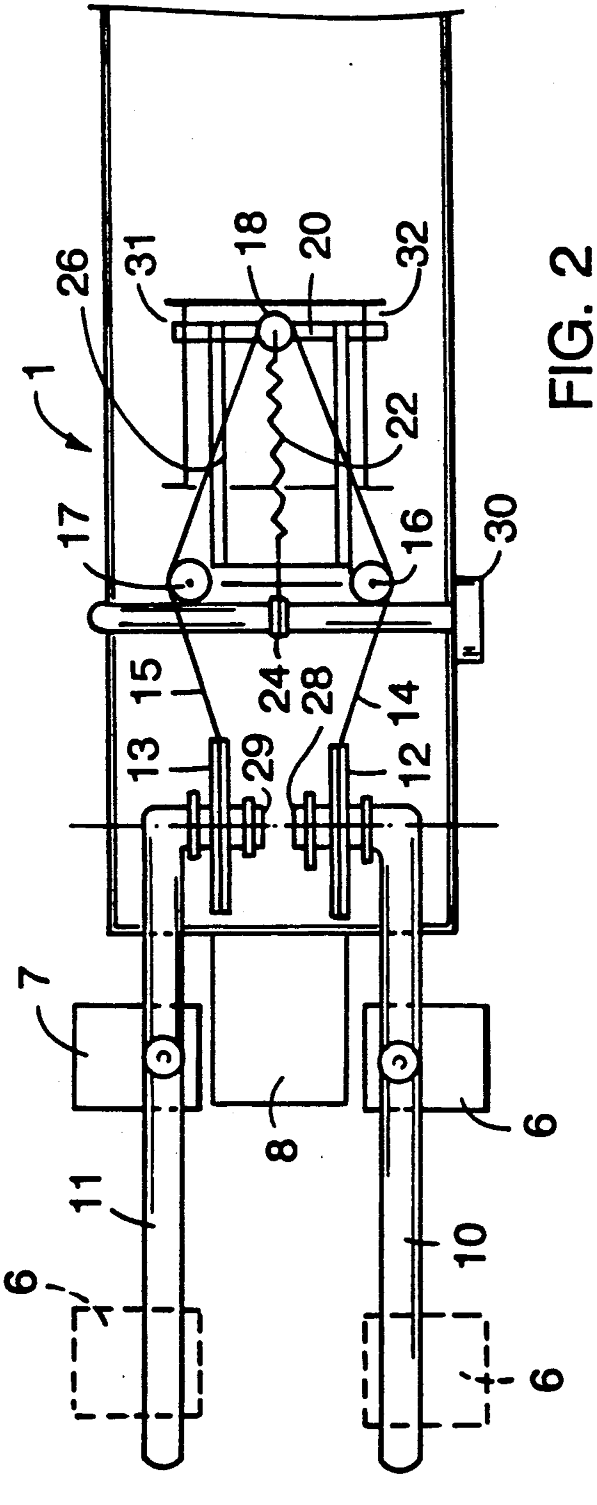
FIG. 2 is a top view of the invention.

With reference to FIGS. 1 and 2, a posture improvement apparatus of this invention is shown at 1. The posture improvement apparatus 1 generally comprises a base 2 having a relatively flat surface 4 for allowing a patient to lie down thereupon. The apparatus 1 also includes a head rest 8 and a movable arm rests 6 and 7.

The head rest 8 extends from a head-end portion of the base 2 and is positioned to receive the head of the patient lying on the flat surface 4. Also extending from the head-end portion of the base 2, and on either side of the head rest 8, are arm rest guard rails 10 and 11. The arm rests 6 and 7 are movably fixed to the guide rails 10 and 11, respectively, and are secured at particular settings along the guide rails 10 and 11 with an adjustment knob 5 associated with each of the arm rests 6 and 7.

As best shown in FIG. 1, the flat surface 4 of the base 2 includes an opening 25 which allows a flexible membrane 26 to protrude from the surface 4. The thoracic spine of the patient lying on surface 4 is positioned so as to rest directly on top of the flexible membrane 26. As will be described hereinafter, the middle or lower trapezius muscles of the back of the patient may be isolated by varying the position of the arm rests 6 and 7 along the guide rails 10 and 11. It will be appreciated that the extension of the flexible membrane 26 into the back of the patient in fact provides the desired thoracic extension which effectively stretches the appropriate ligaments and muscles.

A pulley and cable system 16 are provided within the apparatus 1 varying the extension of the flexible membrane 26 through the opening 25 of the flat surface 4. Each of the arm rest guide rails 10 and 11 are rotatable about pivot portions 28 and 29, respectively. The pivot portions 28 and 29 have associated therewith pulleys 12 and 13 which are rotatable in response to the guide rails 10 and 11 being lifted or depressed due to the force exerted by the patient's arms. A cable 14 is coupled between the pulley 12 and a movable pulley 18. The cable 14 also comes into contact with a fixed pulley 16 at an intermediate point. A cable 15 is coupled between the pulley 13 and the movable pulley 18, and also comes into contact with a fixed pulley 17 at an intermediate point. The movable pulley 18 is attached atop of a movable attachment member 20 which may be displaced along guides 31 and 32, which run along the length of the apparatus 1.

A spring 22 is disposed between the attachment member 20 and an adjustable attachment member 24. The spring 22 provides mechanical advantage to overcome the inherent resistance of the flexible membrane, and relative weakness of the middle and lower trapezious muscles. The adjustable attachment member 24 is coupled to an adjustment knob 30 which is utilized to increase or decrease the tension associated with the spring 22.

As best shown in FIG. 1, the flexible membrane 26 is attached at one end to a fixed point and at the other end to an attachment member 19 associated with the movable pulley 18.

When in operation, it is typical that a force exerted on the guide rails 10 and 11, by way of the arm rests 6 and 7, will cause the pulleys 12 and 13 to rotate in a counter clockwise direction. As the cables 14 and 15 are pulled in the direction of the head-end of the apparatus 1, it will be appreciated that the movable pulley 18 and the attachment member 20 are forced to be displaced towards the head-end of the apparatus 1. The spring 22 operates to overcome the inherent resistance of the flexible membrane 26 from compressing, and thus from projecting from the opening 25. As the spring 22 is compressed due to the displacement of the attachment member 20, the flexible membrane 26 is increasingly projected in upward increments from the opening 25 of the surface 4 and into the back of the patient. Upon the force being removed from the guide rails 10 and 11, the spring 22 will displace the movable pulley 18 and attachment member 20 back to their original positions, and thus decrease the upward displacement of the flexible membrane 26.

It will be appreciated that the pulley and cable system is a bifurcated system, in that the guide rails 10 and 11 are configured to independently exert forces which displace the movable pulley 18 and the attachment member 20. The separation between the left and right sides of the system is provided to ensure that the exercise motions used in connection with the apparatus I are in fact therapeutic and not dominated by the patient's stronger side.

Figure 4A:
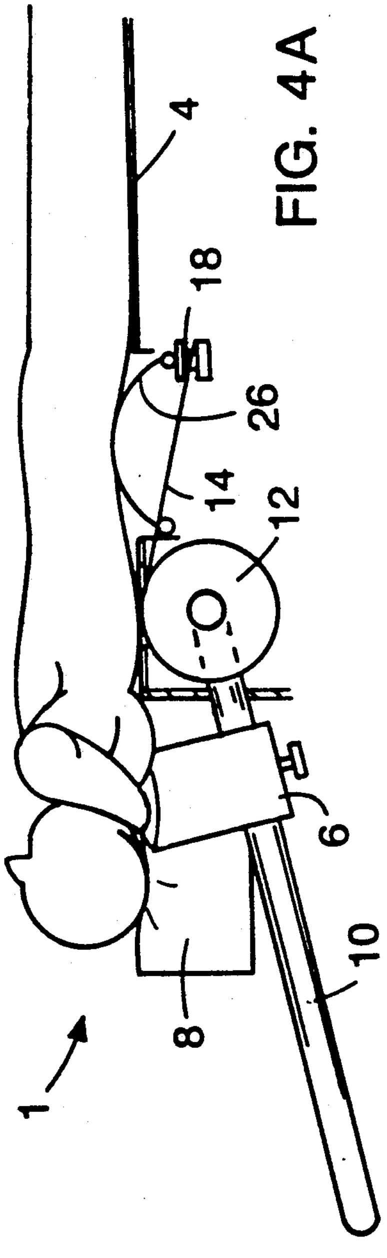
FIG. 4A is a side view illustrating another use of the invention by a patient for posture improvement purposes.
Figure 4B:
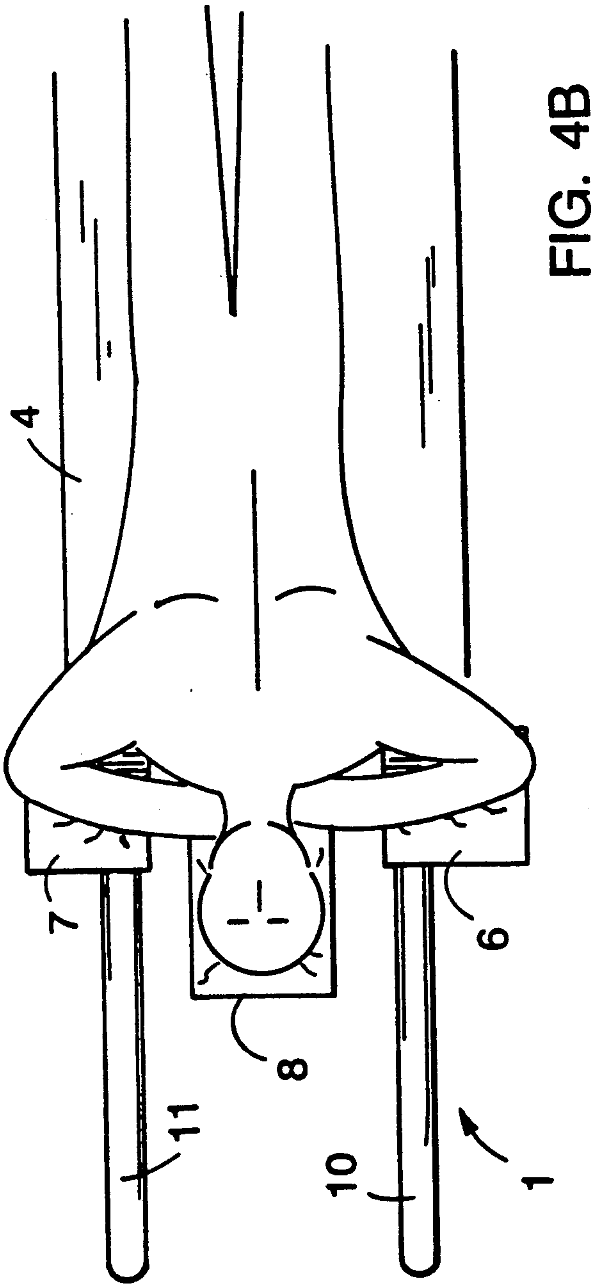
FIG. 4B is a top view another use of the invention by a patient for posture improvement purposes.

With reference now to FIGS. 4A and 4B, one particular use of the apparatus 1 is illustrated. In FIG. 4A, a patient is shown utilizing the apparatus 1 in a manner which isolates the middle trapezius muscles. The patient is reclined on a flat surface 4 with his hands and fingers interlocked behind his neck as shown in FIG. 4B. In this position, the arm rests 6 and 7 are positioned to support the upper forearms and elbows of the patient using the apparatus 1. As force is exerted by the patient on the guide rails 10 and 11 in a downward direction, the pulley 12 is rotated in a counter clockwise direction. As the pulley 12 is rotated in the counter clockwise direction, the cable 14 displaces the movable pulley 18, and thus increases the upward displacement of the flexible member 20 of the patient. The extension of the flexible membrane 26 thus causes, a stretching of the pectoralis minor muscle.

Figure 3A:
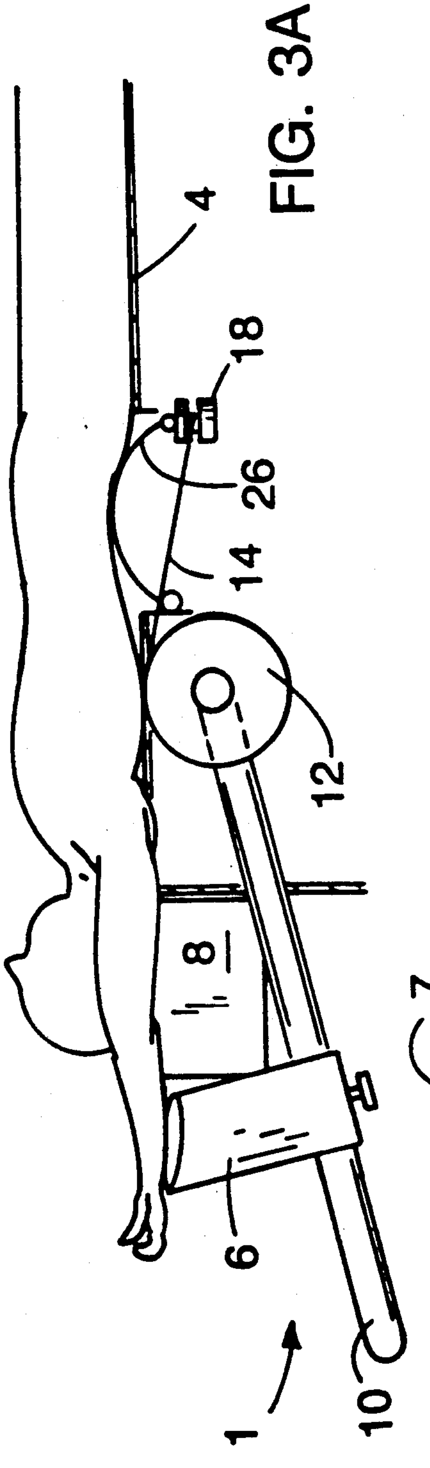
FIG. 3A is a side view illustrating a patient utilizing the invention for posture improvement purposes.
Figure 3B:
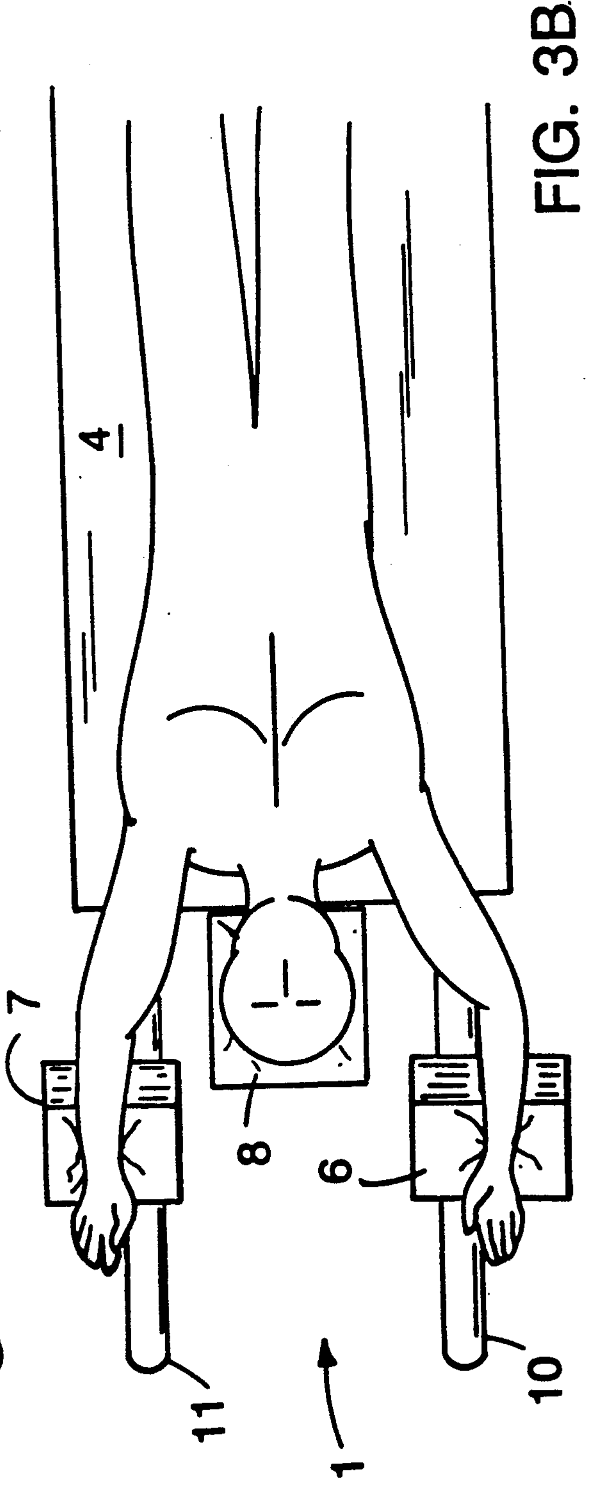
FIG. 3B is a top view illustrating a patient utilizing the invention for posture improvement purposes.

Referring now to FIGS. 3A and 3B, the apparatus 1 is illustrated in use by a patient while isolating the lower trapezius muscles. As shown in FIGS. 4A and 4B, the patient is reclined on the flat surface 4 with arms extended straight overhead with palms facing upward. The arm rests 6 and 7 are positioned along the guide rails 10 and 11 so as to support the lower forearms and wrists of the patient. As the patient applies pressure in the posterior direction to the arm rests 6 and 7, the projection of the flexible membrane 26 is again increased in order to extend into the thoracic spine of the patient.

The apparatus 1 thus provides a means by which the patient can carry out therapeutic active exercise while at the same time receive therapeutic passive motion or extension of the thoracic spine through isolation of the middle and lower trapezius muscles, and further provides exercise to back muscles which will lead to better posture to the patient. Therapeutic correction of the postural fault is accomplished by strengthening the middle and lower trapezius muscles while stretching the pectoralis minor muscle. The rebalancing of these muscles will result in improved posture to the patient.

The invention is not limited to the embodiment disclosed herein and other variations will be apparent to those skilled in the art.

What I claim is:

1. A device for improving posture comprising:

a base having a head-end section and a middle section;

a head support means disposed at said head-end section of said base for supporting the head of a patient lying on said base;

first and second resistance means movably disposed at said head-end section of said base and projecting from said head-end section for supporting the arms of the patient; and extension means disposed at said middle section of said base, said extension means being connected to said first and second movable resistance means so that movement of said first and second resistance means by the patient's arms causes the extension means to be projected in an upward direction at various increments for application of support to a section of the back of the patient, wherein said extension means provides increased thoracic extension to the back of the patient in response to said extension means being projected in upward increments due to the movement of said first and second resistance means.

2. The device according to claim 1, further comprising projection means coupled to said extension means for increasing the projection of said extension means in upward increments.

3. The device according to claim 2, wherein said extension means is a flexible membrane having a proximal end and a distal end and which projects upward in response to being compressed by said projection means.

4. The device according to claim 3, wherein said projection means further comprises:

a spring means having a proximal end and a distal end and being coupled to said flexible membrane, said spring means compressing said flexible membrane in response to said spring means being compressed;

a spring setting means coupled to said proximal end of said spring means for varying the tension associated with said spring means;

a spring attachment means coupled to between said distal end of said spring means and said distal end of said flexible membrane and being movable in the direction of said spring means; and force application means coupled to said spring attachment means for applying an external force to said spring means in order to compress or extend same.

thus compressing or extending said flexible membrane.

5. The device according to claim 4, wherein said force application means is coupled to said first and second resistance means, said first and second resistance means being the source of said external force.

6. The device according to claim 5, wherein said force application means includes first and second sections being coupled to said first and second resistance means, respectively, in order to allow said first and second resistance means to provide independent applications of external force to said spring means.

7. The device according to claim 6, wherein said first and second sections of said force application means each comprise a pulley and cable system coupled between said attachment means and said first and second resistance means, respectively.

8. The device according to claim 1, wherein said first and second resistance means comprise:

first and second arm rests on which the arms of said patient rest while the patient lies on said base; and first and second guide rails on which said arm rests are adjustably coupled, said arm rests being movably set along said guide rails.

* * * * *